United States Patent
Taveras

[11] Patent Number: 5,950,641
[45] Date of Patent: Sep. 14, 1999

[54] DENTAL FLOSS AND TOOTHPICK DISPENSING COMPARTMENT FOR TOOTHBRUSHES

[76] Inventor: Leonidas Taveras, 761 Jericho Rd., Philadelphia, Pa. 19124

[21] Appl. No.: 09/186,806

[22] Filed: Nov. 5, 1998

[51] Int. Cl.⁶ .................................................. A45D 44/18
[52] U.S. Cl. ............................................ 132/309; 132/311
[58] Field of Search ...................... 132/309, 308, 132/311, 321, 324, 325, 328, 329; 206/63.5, 388; 15/167.1; 401/286, 290, 123, 124, 125

[56] References Cited

U.S. PATENT DOCUMENTS

| | | | |
|---|---|---|---|
| 1,711,183 | 4/1929 | Smith | 132/309 |
| 1,847,495 | 3/1932 | Priest | 132/309 |
| 1,849,769 | 3/1932 | Priest | 132/309 |
| 2,233,522 | 3/1941 | Fickle | 132/309 |
| 2,652,949 | 9/1953 | Martin | 132/309 |
| 4,821,752 | 4/1989 | Widlak | 132/309 |
| 4,957,125 | 9/1990 | Yaneza | 132/309 |
| 5,044,386 | 9/1991 | Nelson | 132/309 |
| 5,066,155 | 11/1991 | English et al. | 401/175 |
| 5,097,852 | 3/1992 | Wu | 132/309 |
| 5,348,028 | 9/1994 | Gustavel | 132/309 |
| 5,676,167 | 10/1997 | Garner | 132/309 |
| 5,765,717 | 6/1998 | Gottselig | 221/45 |

*Primary Examiner*—Gene Mancene
*Assistant Examiner*—Pedro Philogene
*Attorney, Agent, or Firm*—Henderson & Sturm

[57] ABSTRACT

A compartment construction including a hollow cylindrical compartment member 20 adapted to be releasably secured to the bottom end 105 of a self-contained toothbrush 100 wherein the compartment member 20 has one interior chamber 25 dimensioned to hold a plurality of toothpicks 50 and another interior chamber 24 dimensioned to receive a spool of dental floss 27.

13 Claims, 1 Drawing Sheet

DENTAL FLOSS AND TOOTHPICK DISPENSING COMPARTMENT FOR TOOTHBRUSHES

BACKGROUND OF THE INVENTION

1. Field of the Invention

This invention relates to the field of self-contained traveling toothbrush constructions in general and in particular to a dispensing compartment for toothbrushes that dispenses both dental floss and a plurality of toothpicks.

2. Description of the Related Art

As can be seen by reference to the following U.S. Pat. Nos. 5,066,155; 5,676,167; 5,097,852; and 5,044,386, the prior art is replete with myriad and diverse self-contained toothbrush construction containing dental floss and at least one U.S. Pat. No. 5,348,028 which shows a toothbrush construction which contains both dental floss and at least one toothpick.

While all of the aforementioned prior art constructions are more than adequate for the basic purpose and function for which they have been specifically designed, thy are uniformly deficient with respect to their failure to provide a simple, efficient, and practical arrangement wherein a separate compartment is removably secured to the end of a self-contained toothbrush such that the dental floss and toothpick dispensing container may be used either in conjunction with the self-contained toothbrush or as an independent entity.

Most individuals have experienced at least one or more instances wherein the use of a self-contained toothbrush would be impractical of not impolite, but a discrete compartment associated with the self-contained toothbrush having a supply of dental floss and toothpicks would be imminently practical.

As a consequence of the foregoing situation, there has existed a long-standing need for a new and improved self-contained toothbrush construction having a detachable compartment that would contain and dispense both dental floss and a supply of toothpicks; and the provision of such a construction is the stated objective of the present invention.

BRIEF SUMMARY OF THE INVENTION

Briefly stated, the compartment construction that forms the basis of the present invention is designed and intended to be releasably secured to the handle portion of a self-contained toothbrush having a toothpaste supply reservoir which forms the handle portion and is in open communication with a hollow toothbrush head element wherein the toothpaste supply is delivered to the toothbrush head element via a conventional plunger mechanism.

As will be explained in greater detail further on in the specification, the compartment construction comprises a generally hollow cylindrical compartment member having an inboard end adapted to be releasably secured to the outboard end of the handle/reservoir portion of the self-contained toothbrush.

In addition, the interior of the compartment member is divided by a partition which divides the interior into an enlarged chamber which contains a reel of dental floss and a smaller chamber that contains the plurality of toothpicks.

Furthermore, the outboard end of the container member is provided with a hinged lid member which serves as a closure for the container; wherein, the hinged lid member is also provided with a severing element that can be employed to separate selective lengths of dental floss from the roll of dental floss.

DETAILED DESCRIPTION OF THE INVENTION

Figure 1:
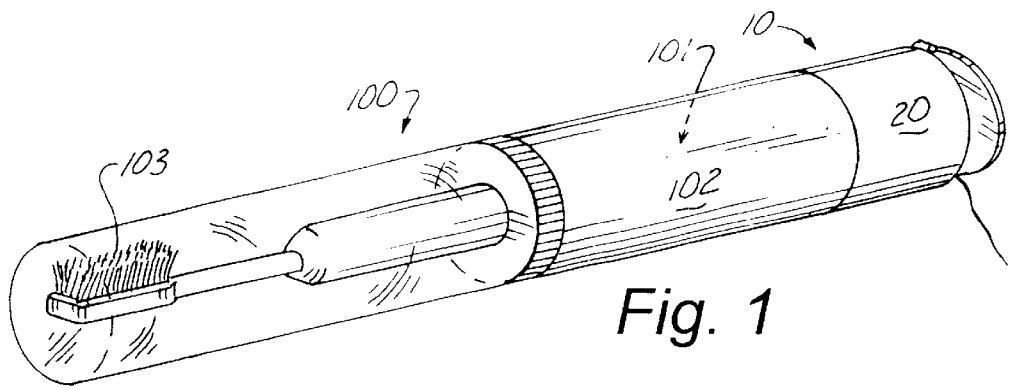
FIG. 1 is a perspective view of the compartment construction that forms the basis of the present invention disposed on the handle portion of a self-contained toothbrush.

As can be seen by reference to the drawings, and particularly to FIG. 1, the compartment construction that forms the basis of the present invention is designated generally by the reference number 10. Furthermore, as shown in FIGS. 1 and 3, the construction 10 is specifically designed to be used both in conjunction with and independently of a self-contained toothbrush designated generally as 100 and including a toothpaste supply reservoir 101 defined by the handle portion 102 of the toothbrush and is in open communication with a hollow toothbrush head element 103; wherein, a plunger element 104 is used to supply toothpaste from the reservoir 101 to the toothbrush head element 103 in a well recognized fashion.

Figure 2:
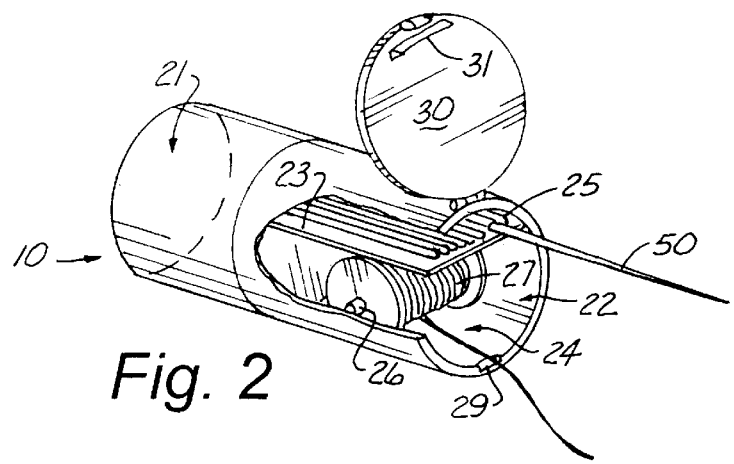
FIG. 2 is an isolated partial cut-away, detailed view of the compartment construction.

As can best be seen by reference to FIG. 2, the compartment construction 10 comprises an elongated generally hollow cylindrical compartment member 20 having a closed end 21 and an open end 22 wherein the interior of the compartment member 20 is provided with a partition 23 which creates an enlarged interior chamber 24 and a reduced size interior chamber 25.

Figure 3:
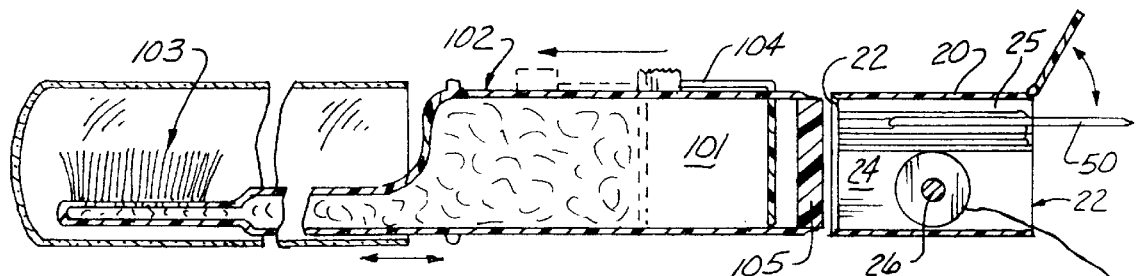
FIG. 3 is a cross-sectional view showing one operative engagement between the compartment construction and a self-contained toothbrush.
Figure 4:
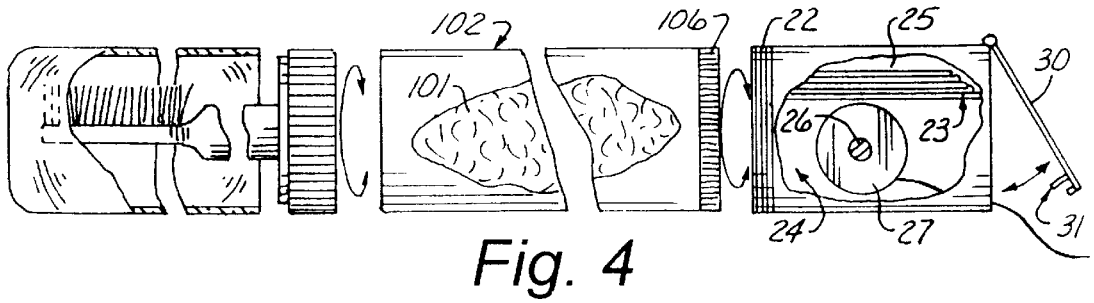
FIG. 4 is a side plan view showing another type of operative engagement between the compartment construction and a self-contained toothbrush.

As shown in FIGS. 2 thru 4, the reduced size interior chamber 25 is dimensioned to receive a plurality of toothpicks 50; whereas, the enlarged interior chamber 24 is provided with a transverse axle element 26 which rotatably supports a spool 27 of dental floss.

In addition, as can be seen by reference to FIGS. 2 and 4, the open end 22 of the container member 20 is provided with a hinged lid member 30 provided with a severing element 31 proximate its free end which is further provided with a discrete notch 32 which cooperates with a complimentary notch 29 in the open end 22 of the compartment member 20 to allow a length of floss to be fed from the interior to the exterior of the compartment member 20; wherein, it can subsequently be severed by the severing element 31.

Turning now in particular to FIGS. 3 and 4, it can be seen that in one version of the preferred embodiment of the invention shown in FIG. 3, the closed end 22 is slightly recessed to frictionally engage a rubber plug 105 provided at the bottom end of the handle portion 102 of the toothbrush 100; and, in the other version of the preferred embodiment of the invention shown in FIG. 4, the closed end 22 of the compartment member 20 is provided with threads that are engaged by the threaded bottom end 106 of the handle portion 102 of the toothbrush 100.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

Having thereby described the subject matter of the present invention, it should be apparent that many substitutions, modifications and variations of the invention are possible in light of the above teachings. It is therefore to be understood that the invention as taught and described herein is only to be limited to the extent of the breadth and scope of the appended claims.

I claim:

1. An improvement in a self-contained toothbrush which comprises a toothpaste supply reservoir defined by the handle portion of the toothbrush wherein the supply reservoir is in open communication with a hollow toothbrush head element formed on one end of the handle portion of the toothbrush wherein the other end of the handle portion of the toothbrush is the bottom end; wherein, the improvement comprises:

a compartment construction including a generally hollow cylindrical compartment member having a closed end, and an open end provided with a hinged lid member; wherein the interior of the compartment member is provided with a partition which divides the interior of the compartment member into two chambers; and means for releasably connecting the closed end of the compartment member to one of the ends of the self-contained toothbrush.

2. The improvement as in claim 1, wherein one of the chambers is dimensioned to receive a supply of toothpicks and the other chamber is provided with a spool of dental floss.

3. The improvement as in claim 2, wherein, said other chamber is provided with an axle element which rotatably supports said spool of dental floss.

4. The improvement as in claim 3, wherein said lid member is provided with a severing element.

5. The improvement as in claim 4, wherein said severing element is disposed proximate to the free end of the lid member.

6. The improvement as in claim 3, wherein said open end of the compartment member is provided with a discrete notch.

7. The improvement as in claim 3, wherein said lid member is provided with a discrete notch.

8. The improvement as in claim 3, wherein both the lid member and the open end of the compartment member are provided with discrete notches.

9. A compartment construction comprising:

an elongated generally hollow cylindrical compartment having a closed end and an open end provided with a hinged lid member; wherein the interior of the compartment member is provided a partition which divides the interior of the compartment member into two chambers wherein one chamber is dimensioned to receive a plurality of toothpicks and the other chamber is dimensioned to receive a spool of dental floss.

10. The construction as in claim 9, wherein said other chamber is provided with an axle element that rotatably supports said spool of dental floss.

11. The construction as in claim 10, wherein said lid member is provided with a severing element.

12. The construction as in claim 10, wherein at least a selected one of the lid member, and the open end of the compartment member is provided with a discrete aperture.

13. The construction as in claim 11, wherein at least a selected one of the lid member and the open end of the compartment member is provided with a discrete aperture.

* * * * *